US00PP08151P

United States Patent [19]

van der Knaap

[11] Patent Number: Plant 8,151

[45] Date of Patent: Feb. 16, 1993

[54] CHRYSANTHEMUM PLANT — BUTTERCUP CULTIVAR

[75] Inventor: Jacques C. M. van der Knaap, De Lier, Netherlands

[73] Assignee: Fides Beheer B.V., De Lier, Netherlands

[21] Appl. No.: 720,731

[22] Filed: Jun. 25, 1991

[51] Int. Cl.[5] ..... A01H 5/00

[52] U.S. Cl. ..... Plt./82.2

[58] Field of Search ..... Plt./74.1, 82.2

*Primary Examiner*—Howard J. Locker

*Attorney, Agent, or Firm*—Burns, Doane, Swecker & Mathis

[57] ABSTRACT

A new and distinct cultivar of Chrysanthemum plant named Buttercup is provided. The new cultivar was the result of a controlled breeding program wherein the Cassa cultivar (U.S. Plant Pat. No. 6,103) was pollinated by the Ahrensia cultivar (non-patented in the United States). More specifically, the new cultivar forms attractive relatively small single intense yellow flowers having a yellow-green disc florets which change to yellow when mature (as illustrated). The inflorescence is pyramidal in configuration and tends to flatten upon maturity. The response period of the flowers is approximately seven and one-half weeks. The plant is both low temperature and high temperature tolerant. The new cultivar is particularly suited for use in the production of a cut single spray under greenhouse conditions.

1 Drawing Sheet

SUMMARY OF THE INVENTION

The present invention comprises a new and distinct cultivar of Chrysanthemum, botanically known as *Chrysanthemum morifolium,* Ramat., and hereinafter is referred to by the cultivar name Buttercup.

The new cultivar is the product of a planned breeding program which had as its objective the creation of a new Chrysanthemum cultivar which exhibits attractive relatively small single flowers having intense yellow ray florets, a flower response period of approximately seven and one-half weeks, tolerance to both low temperatures and high temperatures, and the ability to produce flowers of commercially acceptable quality throughout the year in a cut mum production program. Such combination of traits is not believed to have been present in the previously available Chrysanthemum cultivars. This objective was satisfactorily fulfilled in the cultivar of the present invention.

The breeding program which resulted in the production of the new cultivar of the present invention was carried out in a controlled environment during 1981 at De Lier, The Netherlands. The female parent (i.e., the seed parent) was the Cassa cultivar (U.S. Plant Pat. No. 6,103) and the male parent (i.e., the pollen parent) was the Ahrensia cultivar (non-patented in the United States). The parentage of the new cultivar can be summarized as follows:

CASSA×AHRENSIA.

The seeds resulting from the above pollination were sown and plantelets were obtained which were physically and biologically different from each other. Selective study during July, 1982 resulted in the identification of a single plant of the new variety.

It was found that the new cultivar of the present invention:

(a) exhibits attractive relatively small single flowers having an overall diameter of commonly less than 50 mm. wherein the petals are intense yellow and the disc florets are yellow-green changing to yellow when mature,
(b) bears flowers in a somewhat pyramidal configuration which tends to flatten upon maturity,
(c) exhibits a flower response period of approximately seven and one-half weeks,
(d) exhibits tolerance to both low temperature and high temperature,
(e) forms attractive dark green foliage, and
(f) has the ability to produce flowers of commercially acceptable quality throughout the year in a cut mum production program.

Asexual reproduction of the new cultivar by cuttings initially taken during August, 1982, as performed at De Lier, The Netherlands, in a controlled environment has demonstrated that the characteristics of the new cultivar as herein disclosed are firmly fixed and are retained through successive generations of asexual propagation.

Buttercup has not been observed under all possible environmental conditions to date. Accordingly, it is possible that the phenotype may vary somewhat with variations in the environment, such as temperature, light, day length, contact with pesticides and/or subjection to growth retardant treatments.

When the new cultivar of the present invention is compared to the Cassa Sunny cultivar (non-patented in the United States), the Buttercup cultivar is found to exhibit a smaller flower size (e.g. a flower diameter of approximately 40 to 45 mm. vs. approximately 70 mm.), a more intense yellow coloration of the ray florets, and forms more vegetative growth (e.g., typically assumes a height of approximately 100 cm. vs. approximately 85 cm.). The flower type, response time, and disc floret color of the Buttercup cultivar are substantially identical to those of the Sunny Cassa cultivar.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at De Lier, The Netherlands.

DETAILED DESCRIPTION

The chart used in the identification of colors described hereafter in the R.H.S. Colour Chart of The Royal Horticultural Society, London, England. The color values were determined at 11:00 a.m. to 12:00 noon under natural daylight conditions at De Lier, The Netherlands, on Mar. 13, 1991. The plants described were grown under standard greenhouse conditions which approximate those commonly utilized for the production of cut mums.

Classification:

*Botanical.*—*Chrysanthemum morifolium* Ramat., cv. Buttercup.

*Commercial.*—Cut spray single.

INFLORESCENCE

A. Capitulum:

*Form.*—Pyramidal and tending to flatten upon maturity.

*Type.*—Single.

*Diameter across face.*—Approximately 40 to 45 mm. on average.

*Diameter of flower center.*—Approximately 15 mm. on average.

B. Corolla of ray and disc florets:

*Color (general tonality from a distance of three meters).*—Intense yellow with yellow-green center when immature.

*Color ray florets.*—(top surface) — Intense yellow, Yellow-Orange Group 14A. (under surface) — Intense yellow, Yellow-Orange Group 14B.

*Color disc florets.*—Yellow, Yellow Group 12A when mature and Green Group 142A when immature.

C. Reproductive organs:

*Androecium.*—Present in disc florets.

*Gynoecium.*—Present in disc florets.

PLANT

A. General appearance:

*Height.*—Approximately 100 cm. on average.

B. Foliage:

*Color (upper surface).*—Yellow-Green Group 147A.

*Color (under surface).*—Yellow-Green Group 147B.

*Shape.*—Short-lobed and finely serrated.

I claim:

1. A new and distinct cultivar of Chrysanthemum plant named Buttercup, substantially as herein shown and described, which:

(a) exhibits attractive relatively small single flowers having an overall diameter of commonly less than 50 mm. wherein the petals are intense yellow and the disc florets are yellow-green changing to yellow when mature, (b) bears flowers in a somewhat pyramidal configuration which tends to flatten upon maturity, (c) exhibits a flower response period of approximately seven and one-half weeks, (d) exhibits tolerance to both low temperature and high temperature, (e) forms attractive dark green foliage, and (f) has the ability to produce flowers of commercially acceptable quality throughout the year in a cut mum production program.

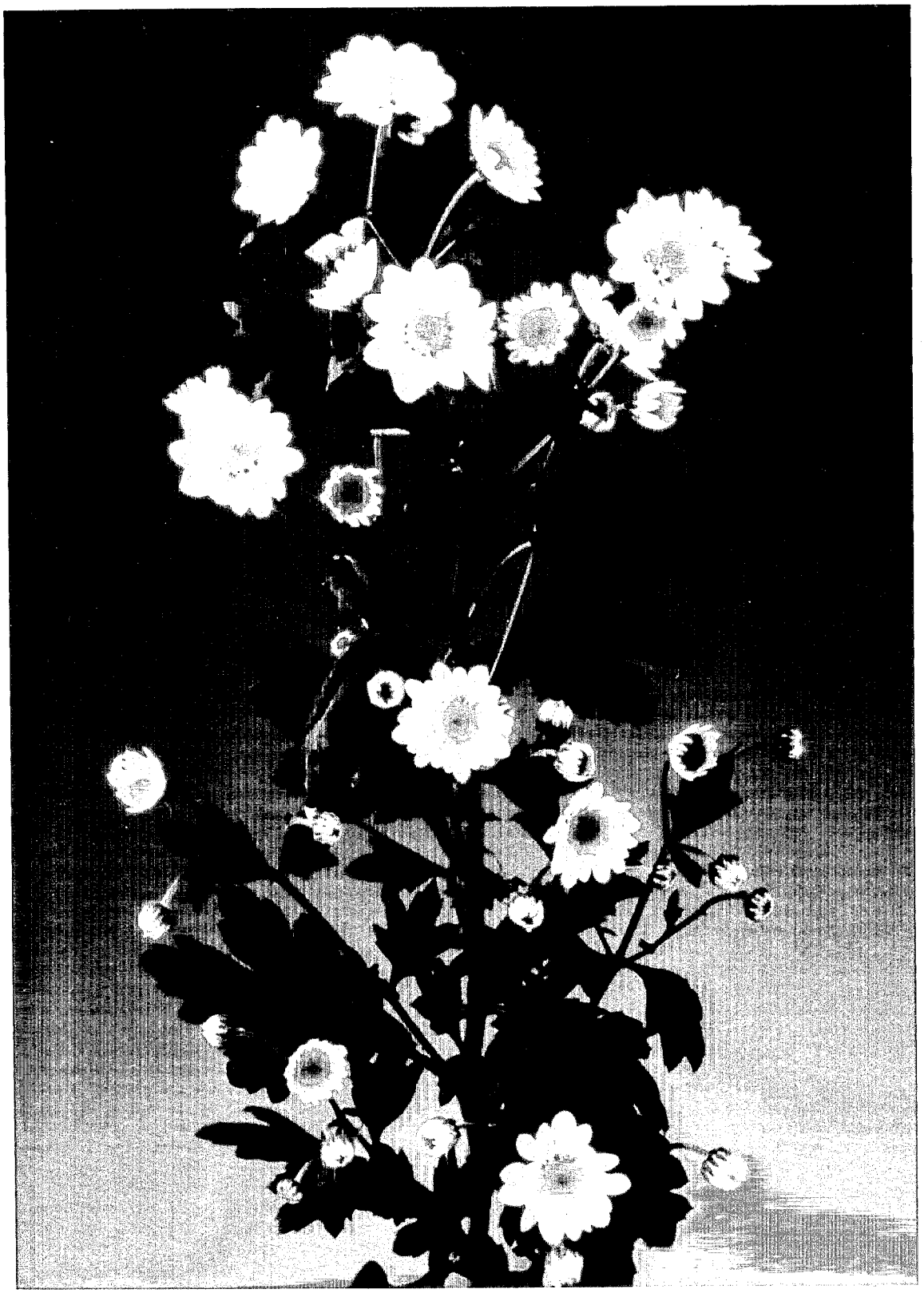

* * * * *